United States Patent [19]

Matterstock et al.

[11] 4,088,474
[45] May 9, 1978

[54] HERBICIDAL AGENTS

[75] Inventors: Karl Matterstock, Hofheim, Taunus; Peter Langeluddeke, Didenbergen, Taunus; Ernst-Friedrich Schulze, Hofheim, Taunus, all of Germany

[73] Assignee: Hoechst Aktiengesellschaft, Frankfurt am Main, Germany

[21] Appl. No.: 566,536

[22] Filed: Apr. 8, 1975

[30] Foreign Application Priority Data

Apr. 10, 1974  Germany ............... 2417487

[51] Int. Cl.² .................. C07C 9/76; A01N 9/24; C07C 65/00
[52] U.S. Cl. ................... 71/108; 71/109; 71/105; 71/106; 71/118; 71/116; 260/465 F; 260/519; 260/520 C; 260/559 B; 260/559 H; 560/57; 560/21; 560/36
[58] Field of Search .......... 260/473 G, 520 C; 71/108, 109, 116

[56] References Cited

U.S. PATENT DOCUMENTS 3,332,957  7/1967  Bencze ............... 260/473 G
3,630,715  12/1971 Guttag ............... 260/473 G Primary Examiner—Paul J. Killos
Attorney, Agent, or Firm—Curtis, Morris & Safford

[57] ABSTRACT

Compounds of the formula

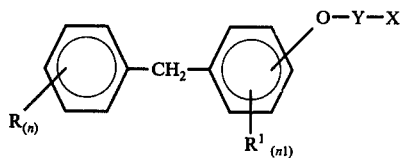

wherein
R is halogen, $(C_1-C_4)$alkyl, halo-$(C_1-C_4)$alkyl, $(C_1-C_4)$alkoxy, halo$(C_1-C_4)$alkoxy, phenyl, $-NO_2$, $-NH_2$ or $-CN$;
R' is $(C_1-C_4)$alkyl or halogen;
n is an integer of from 1 to 3;
$n_1$ is zero or an integer of from 1 to 3;
Y is $(C_1-C_6)$alkylene and
X is $-COOH$, $-COO-(C_1-C_8)$alkyl, $-CONH_2$, $-CONH-NH_2$, $-CN$ or $-COO-Cat$,
"Cat" being the cation of an inorganic or organic base, are useful as selective grass herbicides.

11 Claims, No Drawings

HERBICIDAL AGENTS

The present invention provides benzyl-phenoxyalkanecarboxylic acids and the derivatives thereof corresponding to the formula

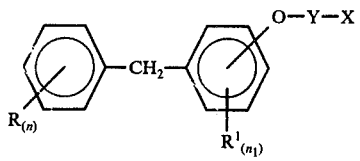    I where
R is halogen, $(C_1-C_4)$alkyl, halo-$(C_1-C_4)$alkyl, $(C_1-C_4)$alkoxy, halo-$(C_1-C_4)$alkoxy, phenyl, —$NO_2$, —$NH_2$ or —CN;
R' is $(C_1-C_4)$alkyl or halogen;
$n$ is an integer of from 1 to 3;
$n_1$ is zero or an integer of from 1 to 3;
Y is $(C_1-C_6)$alkylene and
X is —COOH, —COO—$(C_1-C_8)$alkyl, —$CONH_2$, —CONH—$NH_2$, —CN or —COO—Cat,
"Cat" being the cation of an inorganic or organic base.

In the above formula I, R is preferably halogen, especially chlorine or bromine in 4- or 2,4-position. $n_1$ is preferably zero, that is, the right hand benzene ring is preferably unsubstituted, but may also be substituted by Cl or $CH_3$, $n_1$ in this case preferably being 1. The radical -O-Y-X is preferably in ortho- or para-position, and especially in para-position, to the benzyl radical. Y represents above all the radical —$CH(CH_3)$—. In the case where X is a carboxylic ester group, this group contains preferably from 1 to 4 carbon atoms. "Cat" stands preferably for an alkali or alkaline earth metal cation, especially $Na^+$, $K^+$ or $Ca^{++}/2$.

The benzylphenoxy-alkanecarboxylic acids and the derivatives thereof corresponding to the formula I are prepared according to known methods, for example by reacting benzylphenols of the formula

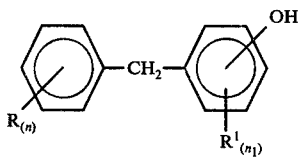    II with halocarboxylic acid derivatives of the formula

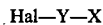    III

Hal—Y—X where Hal is chlorine or bromine and X is —COO—$(C_1-C_8)$alkyl, —$CONH_2$, —CONH—$NH_2$ or —CN.

The reaction is generally carried out in an inert organic solvent such as methanol, ethanol, benzene, petroleum ether, diethylketone, dioxan, DMF or DMSO in the presence of an approximately stoichiometric amount of an inorganic or organic base such as NaOH, KOH, $K_2CO_3$, $Na_2CO_3$, pyridine or triethylamine, at temperatures of from 50° to 150° C, preferably from 80° to 120° C. Subsequently, the free carboxylic acids or the salts thereof may be prepared also in known manner from the reaction products obtained, preferably by saponification of the esters or nitriles.

The starting products of formula II are obtained according to known methods, for example by reaction of a correspondingly substituted benzyl chloride with a phenol in the presence of a condensation agent such as $AlCl_3$ or $ZnCl_3$ (Ind. Eng. Chem. 28, 505 (1936)). In this reaction, benzyl phenols substituted both in o- and p-position are obtained, which may be separated by fractional distillation.

The compounds of formula I have an excellent selective activity against weed grasses. In pre-emergence as well as in post-emergence treatment, such weed grasses are destroyed at low doses, while even considerable overdoses do not or only insignificantly damage broad-leaved (dicotyledonous) crop plants and broad-leaved weeds.

Surprisingly, various crop plants from the botanic species of grasses, for example rice, barley, wheat, sorghum, are not damaged by the compounds of the invention at a dosage sufficient to destroy weed grasses. The compounds may therefore be used for combating weed grasses in cereals as well as in dicotyledonous crop plants such as sugar beet, leguminosae, cotton, vegetables, cucumber species, tomatoes, tobacco etc.

The herbicidal activity is especially pronounced against foxtail grass, wild oat, barnyard grass, foxtail millet, and crabgrass. The compounds may be used before or after the emergence of the plants which is not possible with known herbicides for the selective destruction of weed grasses. Trichloroacetic acid, alachlor (2-chloro-2,6-diethyl-N-(methoxymethyl)-acetanilide) and trifluralin (N,N-di-(n-propyl)-2,6-dinitro-4-trifluoromethylaniline) for example can be used only in pre-emergence treatment; barban (4-chloro-2-butinyl-N-(3-chlorophenyl)-carbamate) or chlorophenpropmethyl (2-chloro-3-(4-chlorophenyl)-propionic acid methyl ester) only in post-emergence treatment. Furthermore, the concentrations required for complete destruction of the weed grasses are considerably lower than with the cited herbicides.

The compounds of the invention may be used in usual formulations, for example as wettable powders, emulsifiable concentrates, sprayable solutions, dusting powders or granules.

Wettable powders are preparations which are homogeneously dispersible in water, and which, in addition to the active ingredient and a diluent or inert substance, contain also wetting agents, for example polyoxethylated alkylphenols, polyoxethylated oleyl or stearyl amines, or alkyl or alkylphenyl-sulfonates, and dispersing agents, for example the sodium salts of lignin-sulfonic acid, 2,2'-dinaphthyl-methane-6,6'-disulfonic acid, dibutyl-naphthalene-sulfonic acid.

Emulsifiable concentrates may be obtained by dissolving the active ingredient in an organic solvent, for example cyclohexanone, xylene, or higher boiling aromatics. In order to obtain a good emulsion in water, further emulsifiers may be added.

Dusting powders are obtained by grinding the active ingredient with finely divided solid substances, for example talcum or natural aluminates, for example kaolin, bentonite, pyrophyllite or diatomaceous earth.

Spraying solutions, commercially available as aerosol sprays, contain the active ingredient dissolved in an organic solvent, and a propellant, for example a mixture of hydrocarbon fluorides.

Granules may be obtained either by atomizing the active ingredient through a nozzle onto an absorptive granulated inert material, or by applying a concentrate of the active ingredient by means of an adhesive, for example polyvinyl alcohol, the sodium salt of polyacrylic acid or mineral oils, onto the surface of a carrier, for example, sand, kaolinites or granulated inert materials. The active substances may also be granulated by the methods used in the preparation of fertilizer granulated material, if desired in admixture with one or more fertilizers.

The concentration of the active substances of the present invention in commercial herbicidal formulations may vary considerably. For example, in wattable powders, the concentration of active ingredient may vary within the range of from about 10% to 50% the remaining amount consisting of the above mentioned formulation additives. In emulsifiable concentrates, the concentration of active ingredient may vary in the range of from about 10% to 50%. Dusting powders generally contain from 5 to 20% and spray solutions from about 3 to 20% of active ingredient. In the case of granules, the content of active ingredient partially depends on whether the active compound is liquid or solid and on what granulating agents, fillers and other additives are used. It is generally from 3 to 10%.

For practical applications, the commercial concentrates are optionally diluted in usual manner, for example, in the case of wettable powders and emulsifiable concentrates, by means of water. Dust formulations, granulated preparations and spray solutions are not diluted any more before their application. The amount of active ingredient required for application varies within wide limits in accordance with the external conditions, for example temperature and moisture; generally from 0.1 to 10.0 kg/ha, preferably from 0.2 to 2.5 kg/ha, of active substances are used.

Examples of formulation:
Wettable powder consisting of
    10–40 wt. % of active substance
    30–40 wt. % of finely dispersed adsorptive silicic acid
    8 wt. % of sodium salt of dinaphthylmethanedisulfonic acid (Tamol$^R$ NNO)
    2 wt. % of sodium salt of alkylnaphthalenesulfonic acid (Leonil$^R$ DB)
    0.5 wt. % of sodium salt of oleylmethyltauride (Hostapon$^R$ T)
remainder    kieselguhr.
Emulsifiable concentrate consisting of
    20–50 wt. % of active substance,
    5 wt. % of calcium salt of dodecylbenzenesulfonic acid
    7 wt. % of nonylphenol-polyglycol ether
    3 wt. % of oleylalcohol-polyglycol ether
remainder    xylene.
Granuled material consisting of
    3–5 wt. % of active substance
    2 wt. % of emulsifier mixture of calcium salt of dodecylbenzenesulfonic acid and castor oil-polyglycol ether / or ester
    5 wt. % of kieselguhr or finely dispersed silicic acid
remainder    quartz sand (0.3 to 1 mm $\phi$).

The novel herbicides may also be combined with known herbicides, for example with the following substances cited by their common names:

| | |
|---|---|
| Urea derivatives: | linuron, monolinuron, chlorotoluron, ipuron, diuron, metoxuron, fluometuron, methabenzthiazuron; |
| Triazine derivatives: | simazine, atrazine, ametryne, prometryne, desmetryne, methoprotryne, metribuzine; |
| Uracil derivatives: | lenacil, bromacil; |
| Pyrazon derivatives: | pyrazone; |
| Phenoxy-alkanecarboxylic acids: | 2,4-D, MCPA, dichloroprop, mecoprop, 2,4-DP, TBA; |
| Carbamic acid derivatives: | barban, phenmedipham, diallate, triallate, vernolate, benthiocarb, Swep; |
| Dinitrophenol derivatives: | dinitro-o-cresol, dinoseb, (DNBP), dinoterb, and the esters or salts thereof; |
| Chlorinated aliphatic acids: | TCA, dalapon; |
| Amides: | diphenamide, isocarbamide; |
| Dipyridilium derivatives: | paraquat, diquat; |
| Anilides: | propanil, solane, monalide, alachlor, propachlor, bentachlor; |
| Anilines: | trifluraline, nitraline, oryzaline, dinitramine; |
| Other active substances: | dichlobenil, ioxynil, cyanazine, pyrazone, bromofenoxim, chlorothalmethyl, benzoylpropethyl, chlorophenpropmethyl, MSMA, DSMA, nitrofen, flurenol, bentazol, fluorodifen. |

The following examples illustrate the invention.

Examples of preparation

EXAMPLE 1

2[p-(4-chlorobenzyl)-phenoxi]-propionic acid ethyl ester.

A solution of 22 g of 4-(4-chlorobenzyl)-phenol and 18.5 g of α-bromopropionic acid ethyl ester in 100 ml of dimethyl formamide was stirred for 2 hours at 100° C together with 16 g of potassium carbonate. After cooling, the reaction mixture was poured into 1 liter of water. An oil precipitated which was separated and dried over sodium sulfate. By means of vacuum distillation, 23.3 g of 2-[p-(4-chlorobenzyl)-phenoxi]-propionic acid ethyl ester were obtained. b.p.: 146° – 151° C/0.1 mm Hg/n$_D^{22}$: 1.5527

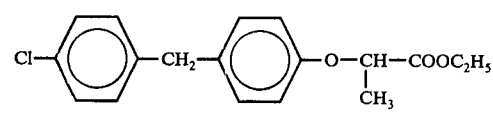

EXAMPLE 2

2-[p-(2,4-dichlorobenzyl)-phenoxi]-propionic acid amide.

A solution of 25.3 g of 4-(2,4-dichlorobenzyl)-phenol and 15.2 g of α-bromopropionic acid amide in 100 ml of dimethyl formamide was stirred for 2 hours at 100° C together with 16 g of potassium carbonate. After cooling, the reaction mixture was poured into 1 liter of water. A viscous oil precipitated which was absorbed in methylene chloride and washed with water. After drying over sodium sulfate, the solvent was distilled off under reduced pressure. The remaining colorless crystals were recrystallized from methanol. Yield: 25.8 g; melting point 148° – 149° C.

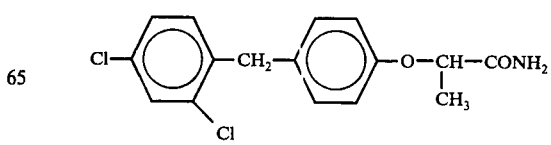

EXAMPLE 3

Sodium salt of 2-[p-(2,4-dichlorobenzyl)-phenoxi]-propionic acid.

17.5 g of 2-[-p-(2,4-dichlorobenzyl)-phenoxi]-propionic acid ethyl ester were stirred with 100 ml of methanol and a solution of 2.5 g of caustic soda in 100 ml of water for 3.5 hours at 50° C, and then abandoned overnight at room temperature. The solvent was distilled off under reduced pressure, and the remaining sodium salt was dried at 60° C under reduced pressure. 19.6 g of sodium salt of 2-[p-(2,4-dichlorobenzyl)-phenoxi]-propionic acid were obtained.

dium sulfate. By vacuum distillation, 16.8 g of 2-[p-(2,4-dichlorobenzyl)-phenoxi]-butyric acid ethyl ester were obtained. b.p. 180° – 183° C/0.8 mm Hg/$n_D^{21}$: 1.5912

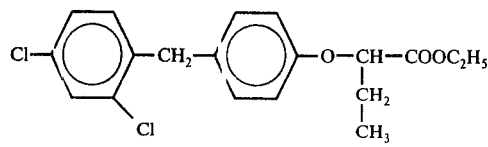

The following compounds were prepared according to the methods described in the above Examples.

Table

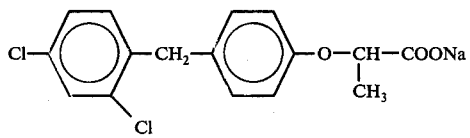

| Ex. No. | R | $R^1$ | Y | Position of the radical —O—Y—X | X | b.p./$n_D$ |
|---|---|---|---|---|---|---|
| 5 | 2,4-Cl | H | —HC(CH₃)— | para | —COOC₂H₅ | 167° C0.1/$n_D^{21}$: 1.5610 |
| 6 | 2-Cl | H | —HC(CH₃)— | " | —COOC₂H₅ | 185° C0.7/$n_D^{22}$: 1.5535 |
| 7 | 2,4-Br | H | —HC(CH₃)— | " | —COOC₂H₅ | 182° /0.05/$n_D^{22}$:15855 |
| 8 | 4-Br | H | —HC(CH₃)— | " | —COOC₂H₅ | 170° /0.1/$n_D^{22}$: 1.5623 |
| 9 | 4-F | H | —HC(CH₃)— | " | —COOC₂H₅ | 135° /0.05/$n_D^{22}$:1.5310 |
| 10 | 4-CHF₂—CF₂—O— | H | —HC(CH₃)— | " | —COOC₂H₅ | 160° /0.05/$n_D^{22}$:1.4945 |
| 11 | 4-Cl | 3-CH₃ | —HC(CH₃)— | " | —COOC₂H₅ | 150° /0.1/$n_D^{20}$:1.5535 |
| 12 | 4-Cl | 2-CH₃ | —HC(CH₃)— | " | —COOC₂H₅ | 152° /0.05/$n_D^{20}$:1.5501 |
| 13 | 4-CH₃ | H | —HC(CH₃)— | " | —COOC₂H₅ | 150° /0.1/$n_D^{23}$: 1.5428 |
| 14 | 4-Phenyl | H | —HC(CH₃)— | " | —COOC₂H₅ | $n_D^{23}$: 1.5834 |
| 15 | 4-CN | H | —HC(CH₃)— | " | —COOC₂H₅ | light brown oil |
| 16 | 4-NO₂ | H | —HC(CH₃)— | " | —COOC₂H₅ | light brown oil |
| 17 | 4-NH₂ | H | —HC(CH₃)— | " | —COOC₂H₅ | medium brown oil |
| 18 | 2,4-Cl | H | —HC(CH₃)— | " | —COOCH₃ | 158° /0.1/$n_D^{22}$: 1.5766 |
| 19 | 2,4-Cl | H | —HC(CH₃)— | " | —COOCH₂—CH(CH₃)(CH₃) | 170° /0.1/$n_D^{22}$: 1.5478 |
| 20 | 2,4-Cl | H | —HC(CH₃)— (with HCH branch) | " | —COOC₂H₅ | 175° /0.1/$n_D^{22}$: 1.5725 |
| 21 | 2,4-Cl | H | —CH₂CH₂— | " | —COOC₂H₅ | 191° /2/ $n_D^{20}$: 1.6177 |
| 22 | 2,4-Cl | H | —CH₂CH₂CH₂— | " | —COOC₂H₅ | 180° /1/ $n_D^{21}$: 1.6106 |
| 23 | 3-CF₃ | H | —HC(CH₃)— | " | —COOC₂H₅ | 132° /0.1/$n_D^{23}$: 1.5028 |
| 24 | 2,4-Cl | H | —HC(CH₃)— | " | —CN | 180° /0.3/$n_D^{22}$: 1.5788 |
| 25 | 2,4-Cl | H | —HC(CH₃)— | " | —CONH—NH₂ | $n_D^{23}$: 1.5849 |
| 26 | 2,4-Cl | H | —HC(CH₃)— | " | —COOCa/₂ | |
| 27 | 3,4-Cl | H | —HC(CH₃)— | " | —COOC₂H₅ | 170° /0.05/$n_D^{23}$: 5622 |
| 28 | 2,4-Cl | 2-Cl | —HC(CH₃)— | " | —COOC₂H₅ | 180° /0.1/$n_D^{22}$: 1.5665 |
| 29 | 2,4-Cl | H | —HC(CH₃)— | ortho | —COOC₂H₅ | 156° /0.1/$n_D^{21}$: 1.5553 |
| 30 | 2,4-Cl | H | —HC(CH₃)— | para | —COO-n-C₆H₁₃ | $n_D^{24.5}$:1.5372 |
| 31 | 2,4-Cl | H | —HC(CH₃)— | " | —COO-n-C₈H₁₇ | $n_D^{24.5}$:1.5255 |
| 32 | 2,4-Cl | 2,6-CH₃ | —HC(CH₃)— | " | —COOC₂H₅ | 153° /0.01/$n_D^{22}$: 1.5663 |

EXAMPLE 4

2-[p-(2,4-dichlorobenzyl)-phenoxi]-butyric acid ethyl ester.

A solution of 25.3 g of 4-(2,4-dichlorobenzyl)-phenol and 15 g of α-chlorobutyric acid ethyl ester in 100 ml of dimethyl formamide were stirred for 2 hours at 100° C with 16 g of potassium carbonate. After cooling, the reaction mixture was poured into 1 liter of water. An oil precipitated which was separated and dried over so-

EXAMPLE 33

2-[p-(2,4-dichlorobenzyl)-phenoxi]-propionic acid.

17.5 g of 2-[p-(2,4-dichlorobenzyl)-phenoxi]-propionic acid ethyl ester were refluxed for 2 hours with a solution of 2.5 g of caustic soda in 100 ml of methanol. After cooling, 100 ml of water were added and the mixture was acidified with 2n hydrochloric acid. The propionic acid liberated precipitated in the form of a colorless oil which, on cooling in icewater, solidified to become a colorless wax-like mass. The yield is 15.3 g.

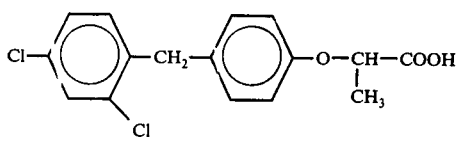

Biological Examples

EXAMPLE I

Seeds of weeds belonging to different botanic families were sown in pots and covered with earth. The same day, the earth was sprayed with wettable powder formulations suspended in water of the compound of Example 5; in similar manner, the known substance dichloroprop[2-(2',4'-dichlorophenoxy)propionic acid] was used as comparative agent. In a further test, both the cited substances were sprayed onto plants already emerged and having developed 2 to 3 leaves.

The results (and also the results of all following tables) were evaluated according to the following scheme in degree of damage in per cent:

| number | weeds | | | crop plants | | |
|---|---|---|---|---|---|---|
| 1 | 100 | | | 0 | | |
| 2 | 97.5 | to | 100 | 0 | to | 2.5 |
| 3 | 95.0 | to | 97.5 | 2.5 | to | 5.0 |
| 4 | 90.0 | to | 95.0 | 5.0 | to | 10.0 |
| 5 | 85.0 | to | 90.0 | 10.0 | to | 15.0 |
| 6 | 75.0 | to | 85.0 | 15.0 | to | 25.0 |
| 7 | 65.0 | to | 75.0 | 25.0 | to | 35.0 |
| 8 | 32.5 | to | 65.0 | 35.0 | to | 67.5 |
| 9 | 0 | to | 32.5 | 67.5 | to | 100 |

In this scheme number 4 is still considered an acceptable herbicidal effect in weeds and satisfactory preserving effect in crop plants (cf. Bolle, Nachrichtenblatt, des Deutschen Pflanzenschutzdienstes 16. 1964, pages 92 – 94).

The results of the following Table I show that the compound of the invention, contrary to dichloroprop, is not or nearly not active against broad-leaved weeds, even at a high dosage rate of 2.5 kg/ha. Its special activity is limited to species of the family of grasses, as demonstrated by the example Lolium, Alopecurus and Echinochloa. Dichloroprop, on the other hand, shows no activity against the cited species and other grasses, which proves that the substances of the invention have a completely different activity spectrum than the known growth herbicides of the dichloroprop type, although being of similar chemical structure.

Table I

Activity against weeds and weed grasses; pot test in a greenhouse; dosage rate: 2,5 kg/ha of A.S. (= active substance)

| plant species | pre-emergence treatment, | | post-emergence treatment | |
|---|---|---|---|---|
| | product of Ex. 5 | dichloroprop | product of Ex. 5 | dichloroprop |
| A. Weeds (dicotyledonous species) | | | | |
| Galium | 8 | 2 | 9 | 2 |
| Matricaria | 8 | 5 | 8 | 4 |
| Ipomoca | 9 | 2 | 9 | 3 |
| Sinapis | 9 | 1 | 8 | 1 |
| Amaranthus | 6 | 1 | 7 | 1 |
| B. Weed grasses (monocotyledonous species) | | | | |
| Lolium | 1 | 9 | 4 | 9 |
| Alopecurus | 2 | 9 | 2 | 9 |
| Echinochloa | 1 | 9 | 1 | 9 |

Table I-continued (above)

EXAMPLE II

Seeds of wheat, barley, foxtail grass (Alopecurus myosuroides) and wild oat (avena aftua) were sown in pots and allowed to emerge in a greenhouse; after having developed 3 to 4 leaves they were sprayed with aqueous suspensions of substances of the invention. As comparative agent, the commercially available compound chlorophenpropmethyl was used.

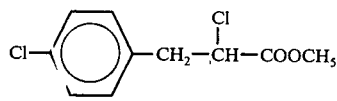

The results listed in Table II show that 4 weeks after the treatment, foxtail grass and wild oat were substantially destroyed by the compounds of the invention, already at low dosage rates of, for example, 0.62 kg/ha, while the crop plants were not or only very slightly damaged. Chlorophenpropmethyl, on the other hand, damaged wild oat only slightly at the high dosage rate of 1.25 kg/ha, while foxtail grass remained entirely undamaged.

Table II

Pot test in the greenhouse; post-emergence treatment dosage rates in kg/ha of A.S.

| plant species | Chlorophenpropmethyl | | product according to Example | | | |
|---|---|---|---|---|---|---|
| | | | No. 5 | | No. 7 | |
| | 1.25 | 0.62 | 1.25 | 0.62 | 1.25 | 0.62 |
| A. Weed grasses | | | | | | |
| Alopecurus myosuroides | 9 | 9 | 1 | 1 | 1 | 1 |
| Avena fatua | 4 | 8 | 1 | 2 | 3 | 4 |
| B. Crop plants | | | | | | |
| Wheat | 1 | 1 | 1 | 1 | 1 | 1 |
| Barley | 1 | 1 | 4 | 2 | 2 | 1 |

The compounds of Examples 18, 19, 30 and 31 had a similar activity as those of Examples 5 and 7.

EXAMPLE III

Barnyard grass (Echinochloa) is one of the most important weeds in rice cultures of rice cultivating countries, both when the rice is directly sown as well as when it is reared in plant nurseries and then transplanted. The two following tests A and B prove that the substances of the invention are most suitable for combating barnyard grass in rice planted according to both cultivating methods.

In test A, barnyard grass and rice were sown in pots simultaneously. After the plants had developed 3 to 4 leaves, the invention compounds in the form of aqueous suspensions were sprayed onto the plants. The result indicated in Table III (4 weeks after the treatment) shows that the lowest dosage rate (0.31 kg/ha of active substance) of all substances is sufficient to combat the barnyard grass; a double dosage of substances of the invention does not seriously damage the rice.

In test B, 3 weeks old rice plants were transplanted into pots and simultaneously, barnyard grass was sown. A few days later, when the barnyard grass began to emerge, the pots were flooded, and the invention compounds were added to the stagnant water. The results obtained 4 weeks after the treatment are shown in Table III.

Table III

Test in flooded pots in the greenhouse; dosage rates in kg/ha of A.S.

| Plant species | products of Examples | | | |
|---|---|---|---|---|
| | No. 5 | | No. 7 | |
| | 0.62 | 0.31 | 0.62 | 0.31 |
| Test A | | | | |
| Simultaneous sowing of Echinochloa and rice; | | | | |
| Treatment: spraying after emergence | | | | |
| Echinochloa | 1 | 3 | 1 | 2 |
| rice | 2 | 1 | 2 | 1 |
| Test B | | | | |
| Sowing of Echinochloa at the time of transplanting the rice, | | | | |
| Treatment: Addition of the products to the stagnant water | | | | |
| Echinochloa | 2 | 2 | 1 | 4 |
| rice | 1 | 1 | 1 | 1 |

EXAMPLE IV

In regions where there is a crop rotation of soybeans after corn (for example in wide areas of the U.S.A.), volunteer corn in soybeans is a serious problem. In order to test whether substances of the invention are suitable for combating corn in soybeans, corn and soybeans were sown in pots and, after emergence, treated with aqueous suspensions of substances of the invention. (See Table IV). The results listed in Table IV show that the compounds of the invention used for this purpose destroy the undesirable corn plants without damaging the soybeans.

Table IV

Pot test in the greenhouse; post-emergence treatment dosage rate: 2,5 kg/ha of A.S.

| Plant species | product of Examples | | | |
|---|---|---|---|---|
| | No. 5 | No. 19 | No. 18 | No. 7 |
| A. Weed grasses | | | | |
| Zea mays | 1 | 3 | 3 | 4 |
| B. Crop plant | | | | |
| Soybean | 1 | 1 | 1 | 1 |

EXAMPLE V

In a further test, seeds of the barnyard grass (Echinochloa) and foxtail millet (Setaria) as well as of sorghum and cotton were sown. After emergence, the plants were sprayed with aqueous suspensions of substances of the invention (see Table V).

The results show that substances of the invention, at dosage rates of 0.31 and 0.62 kg/ha, have a good to very good destructive effect on the cited weed grasses without damaging sorghum and cotton.

Table V

Pot test in the greenhouse; post-emergence treatment dosage rates in kg/ha of A.S.

| Plant species | product of Examples | | | |
|---|---|---|---|---|
| | No. 5 | | No. 7 | |
| | 0.62 | 0.31 | 0.62 | 0.31 |
| A. Weed grasses | | | | |
| Echinochloa | 1 | 2 | 1 | 1 |
| Setaria | 1 | 3 | 1 | 5 |
| B. Crop plant | | | | |
| Sorghum vulgare | 2 | 1 | 2 | 1 |
| Cotton | 1 | 1 | 1 | 1 |

EXAMPLE Va

Compounds 5 and 7 were sprayed in form of aqueous suspensions at a dosage rate of 2.5 kg/ha of active substance onto a number of crop plants in the stage of 2 to 3 leaves. The following species were not damaged: sugar beet, common beet, spinach, cucumber, sugar melon, water melon, red clover, lucerne, peanut, soybean, dwarf-bush bean, pea, horse bean, flax, carrot, celery, rape, cabbage, tomatoe, tobacco, potatoe, cotton. This test proves that substances of the invention may be used in dicotyledonous crop plants even at high dosage rates without a risk for the crop plants.

EXAMPLE VI

Seeds of crabgrass (Digitaria), wild oat (Echinochloa) and foxtail millet (Setaria), as well as of sorghum were sown in pots. The same day, substances of the invention in the form of aqueous suspensions were sprayed at different dosage rates on the soil surface (pre-emergence treatment). The result indicated in Table VI shows that substances of the invention, at dosage rates of 0.31 or 0.62 kg/ha, destroy the cited weed grasses, and that they do not damage substantially the sorghum at the same time, nor when they are used in a high concentration of 1.25 kg/ha. The comparative agent, that is, commercial alachlor

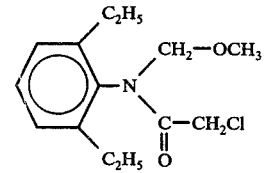

generally used in the agricultural practice for combating grasses in the pre-emergence treatment with very good success damaged the sorghum to such an extent that it practically cannot be used in this crop plant. The comparative agent propachlor

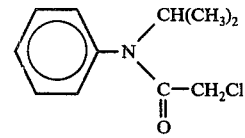

also a known commercial herbicide, had to be used at a much higher dosage rate; even at 1.25 kg/ha, the weed grasses were not completely destroyed.

EXAMPLE VII

In a similar test, two substances of the invention were examined for their action against foxtail grass (Alopecurus) in cereals. The result indicated in Table VII proves that both these substances are suitable for selectively combating foxtail grass in cereals.

EXAMPLE VIII

In further tests, seeds of the weed grasses listed in Table IX were sown in pots, and subsequently, the earth was sprayed with an aqueous suspension of the compounds of the invention. The damage values cited in Table IX were obtained 4 weeks after the application. The data show that the substances of the invention have a good herbicidal activity against the weed grasses used in the test, that is, foxtail grass (Alopecurus), foxtail millet (Setaria), meadow-grass (Poa spec.), ray-grass (Lolium) and barnyard grass.

Table VI

Pot test in the greenhouse; pre-emergence treatment; dosage rates in kg/ha of A.S.

| plant species | Propachlor 1.25 | Alachlor 1.25 | Alachlor 0.62 | Alachlor 0.31 | product of Ex. No. 5 1.25 | product of Ex. No. 5 0.62 | product of Ex. No. 5 0.31 |
|---|---|---|---|---|---|---|---|
| A. Weed grasses | | | | | | | |
| Digitaria | 4 | 1 | 1 | 1 | 1 | 1 | 2 |
| Echinochloa | 2 | 1 | 1 | 2 | 1 | 3 | 4 |
| Setaria | 6 | 3 | 5 | 7 | 1 | 1 | 4 |
| B. Crop plant | | | | | | | |
| Sorghum | 3 | 8 | 7 | 4 | 4 | 2 | 1 |

Table VII

Pot test in the greenhouse; pre-emergence treatment; dosage rates in kg/ha of A.S.

| Plant species | product of Example No. 5 1.25 | 0.62 | 0.31 |
|---|---|---|---|
| A. Weed grass | | | |
| Alopecurus | 1 | 2 | 4 |
| B. Crop plant | | | |
| Autumn wheat | 2 | 1 | 1 |
| Autumn barley | 3 | 1 | 1 |

Table VIII

Pot test in the greenhouse; pre-emergence treatment; dosage rate 2,5 kg/ha of A.S.

| Weed grasses | Product of Example 1 |
|---|---|
| Alopecurus | 3 |
| Setaria | 3 |
| Poa spec. | 2 |
| Lolium | 4 |
| Echinochloa | 1 |

The compounds of Examples (6), (8), (13), (23), (2), (3), (26) and (29) had a similar effect.

We claim:

1. A benzyl-phenoxyalkanecarboxylic acid or derivative thereof corresponding to the formula

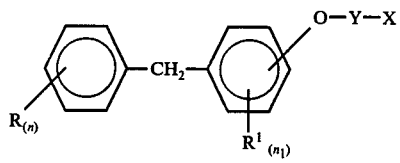

wherein
R is halogen or alkyl, haloalkyl, alkoxy or haloalkoxy of 1 to 4 carbon atoms;
R' is alkyl of 1 to 4 carbon atoms or halogen;
n is an integer of from 1 to 3;
$n_1$ is an integer of from 0 to 3;
Y is alkylene of 1 to 6 carbon atoms and
X is —COOH, —COO alkyl of 2 to 9 carbon atoms or —COO—Cat, "Cat" being the cation of an inorganic or organic base.

2. A compound of claim 1 in which the group —O—Y—X is in para-position relative to the benzyl portion.

3. The compound of claim 1 which is

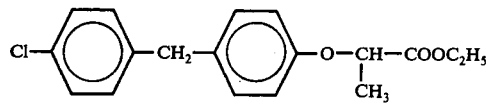

4. The compound of claim 1 which is

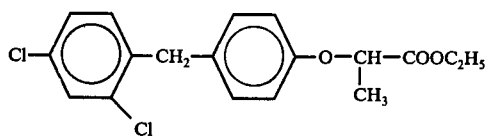

5. The compound of claim 1 which is

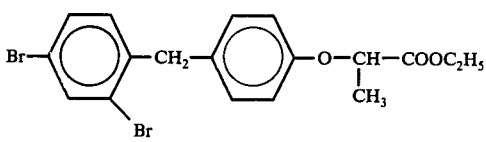

6. The compound of claim 1 which is

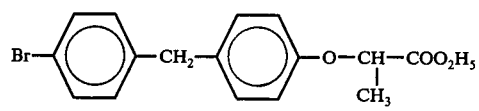

7. The compound of claim 1 which is

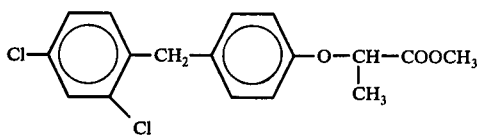

8. The compound of claim 1 which is

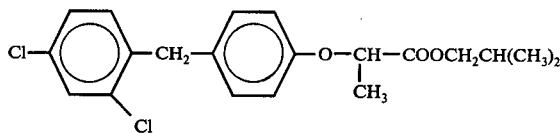

9. The compound of claim 1 which is

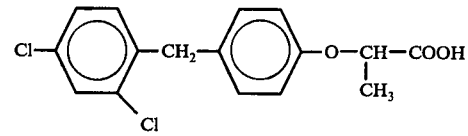

10. A herbicide which comprises an inert carrier and a compound of formula I as claimed in claim 1 as its essential active ingredient.

11. A process for selectively combating weed grasses in crop plants, which comprises applying an active amount of a compound defined in claim 1 to the crop plant to be treated.

* * * * *